(12) United States Patent
Ishiwatari

(10) Patent No.: US 6,169,081 B1
(45) Date of Patent: Jan. 2, 2001

(54) PESTICIDAL DEVICE

(75) Inventor: Takao Ishiwatari, Toyonaka (JP)

(73) Assignee: Sumitomo Chemical Company, Limited, Osaka (JP)

( * ) Notice: Under 35 U.S.C. 154(b), the term of this patent shall be extended for 0 days.

(21) Appl. No.: 09/112,017

(22) Filed: Jul. 8, 1998

(30) Foreign Application Priority Data

Aug. 6, 1997 (JP) .................................................... 9-211570
Jan. 6, 1998 (JO) .................................................. 10-000830

(51) Int. Cl.$^7$ ........................ A01N 65/00; A01N 57/00; A01N 37/00; A01N 37/10; A01N 25/00
(52) U.S. Cl. ........................ 514/65; 514/124; 514/506; 514/529; 514/532; 424/405
(58) Field of Search ............................. 514/124, 65, 506, 514/529, 532; 424/405

(56) References Cited

U.S. PATENT DOCUMENTS

| | | | |
|---|---|---|---|
| 4,551,546 | 11/1985 | Punja | 560/124 |
| 4,714,712 | 12/1987 | Matsuo et al. | 514/531 |
| 4,985,457 | 1/1991 | Kishino et al. | 514/531 |
| 5,163,994 | * 11/1992 | Klimesch et al. | 71/91 |

FOREIGN PATENT DOCUMENTS

| | | | |
|---|---|---|---|
| 07-925581 | 4/1985 | (EP) . | |
| 0 792 581 A1 | * 9/1997 | (EP) | A01N 25/18 |

\* cited by examiner

*Primary Examiner*—Jose' G. Dees
*Assistant Examiner*—Alton Pryor
(74) *Attorney, Agent, or Firm*—Birch, Stewart, Kolasch & Birch, LLP

(57) ABSTRACT

A pesticidal device which comprises a pesticidal ingredient being volatile at room temperature (e.g. 1-ethynyl-2-methyl-2-pentenyl 3-(2-chloro-2-fluorovinyl)-2,2-dimethylcyclopropanecarboxylate, 1-ethynyl-2-fluoro-2-pentenyl 3-(2,2-dichlorovinyl)-2,2-dimethylcyclopropanecarboxylate), 2,3,5,6-tetrafluoro-4-methylbenzyl 3-(2-methyl-1-propenyl)-2,2-dimethylcyclopropanecarboxylate, 2,3,5,6-tetrafluoro-4-methylbenzyl 3-(2-chloro-2-fluorovinyl)-2,2-dimethylcyclopropanecarboxylate, 2,3,5,6-tetrafluoro-4-methylbenzyl 3-(1-propenyl)-2,2-dimethylcyclopropanecarboxylate) is supported on balloon material, and a method for controlling pests by using the pesticidal device.

9 Claims, No Drawings

PESTICIDAL DEVICE

BACKGROUND OF THE INVENTION

The present invention relates to a pesticidal device which needs no heating sources like electric heaters for mosquito-mats.

The pesticidal methods are known at present using mosquito-mats and liquids with absorptive wick. However, these methods need heating sources and they are usually applied in rooms with electric outlet.

DETAILED DESCRIPTION OF THE INVENTION

The object of the present invention is to provide a pesticidal device which needs no heating sources and is available even in the room without an electric outlet.

The present invention is a pesticidal device where a pesticidal ingredient being volatile at room temperature is supported on a balloon material. A loss of the supported pesticidal ingredient by volatilization is small as the surface area of the pesticidal device is also small at the unused time. However, the pesticidal device can exhibit its excellent pesticidal effect by volatilizing its pesticidal ingredient effectively as the surface area of the balloon is swollen to a larger surface area at its used time.

The possible present pesticidal ingredients, which are volatile at room temperature, usually have $1\times10^{-5}$ mmHg or higher, and preferably about $1\times10^{-4}$ to about $1\times10^{-1}$ mmHg at 20° C. Typical examples include pyrethroid compounds such as 1-ethynyl-2-methyl-2-pentenyl 3-(2-chloro-2-fluorovinyl)-2,2-dimethylcyclopropanecarboxylate, 2,3,5,6-tetrafluoro-4-methylbenzyl 3-(2-methyl-1-propenyl)-2,2-dimethylcyclopropanecarboxylate, 2,3,5,6-tetrafluoro-4-methylbenzyl 3-(2-chloro-2-fluorovinyl)-2,2-dimethylcyclopropanecarboxylate, 2,3,5,6-tetrafluoro-4-methylbenzyl 3-(1-propenyl)-2,2-dimethylcyclopropanecarboxylate, 1-ethynyl-2-fluoro-2-pentenyl 3-(2,2-dichlorovinyl)-2,2-dimethylcyclopropanecarboxylate, 1-ethynyl-2-methyl-2-pentenyl 3-(2,2-dichlorovinyl)-2,2-dimethylcyclopropanecarboxylate, empenthrin, transfluthrin, terallethrin, tefuramethrin, furamethrin, tefluthrin, prallethrin, allethrin, and so on; organophosphorus compounds such as fenitrothion, dichlorvos, and so on; carbamate compounds such as BPMC, methoxadiazon, methomyl, and so on; juvenile hormone-like compounds such as methoprene, hydroprene, and so on; pest-repellent compounds such as 3,4-carandiol, N,N-diethyl-m-toluamide, 1-methylpropyl 2-(2-hydroxyethyl)-1-piperidinecarboxylate, p-menthan-3,8-diol, plant essential oil (e.g. hyssop oil), and so on.

The "balloon" used in the present invention means a swollen subject by gas poured inside, usually toy balloon and balloon-like subject. The "balloon material" of the present invention means a subject which can be swollen to balloon by gas.

The quality of the present balloon material is not limited and include rubber, paper, resin (e.g. polyethylene, cross-liked polyethylene, polypropylene, cellophane, polyvinylidene chloride, polyvinyl chloride, polyester, polyvinyl acetal, nylon, fluorocarbon resin, polycarbonate, copolymers thereof, etc.), and aluminium. Rubber and paper are preferably used. A rubber balloon or a paper balloon on the market can be used for the present invention and paper balloon folded by paper craft may also be used.

The shape of the balloon is unlimited and include not only sphere, ellipsoid and discus and animal shapes such as mouse, rat, rabbit and fish. Especially, the balloon of mouse head or tropical fish may ornament the room as well as control pests.

The present pesticidal device is produced by first making a pesticidal ingredient which is volatile at room temperature, and then supporting it on a balloon material by painting or soaking. If necessary, the pesticidal ingredient may be prepared for the device by dissolving it into organic solvents such as acetone, alcohols (e.g. methanol, ethanol, isopropyl alcohol, etc.), aliphatic hydrocarbons, naphthenes, and so on. Further, the present pesticidal device can also produced by forming a paper, rubber, resin, and so on, complex holding the pesticidal ingredient which is volatile at room temperature in advance, then constructing the balloon or applying it to a prepared balloon.

The amount of the pesticidal ingredient which is volatile at room temperature supported on the present pesticidal device is suitably decided depending on the kind of the pesticidal ingredient, size of the balloon material, place to be used, species of the targeted pest, and so on. Typically, about 0.1 to 100 g of the pesticidal ingredient is held per one balloon.

The present pesticidal device may be swollen by pouring air, nitrogen, hydrogen, helium, or other gases, and may be used indoors such as in houses, offices, cotes, warehouses, factories, etc., and outdoors. Moreover, it is also used in cars, and so on. The number of necessary pesticidal devices depends on the size of the pest control area and the degree of pest generation. It is effective to use one to scores of the present pesticidal devices suitably decided by considering such conditions of the environment.

The size of the balloon is usually about 10 cm to about 50 cm in diameter and one to ten balloons of the present invention are usually used in a room.

When the present pesticidal device is used indoors such as in houses or offices, a rubber balloon device swollen by pouring the gas lighter than air (e.g. hydrogen, helium, etc.) is preferable, because it can be floated onto the ceiling and not occupy any floor space. The present pesticidal device swollen by air can also be used without obstruction by hanging the device on the ceiling or by any other method.

The present pesticidal device is effective for controlling various pests including sanitary insects, wood-harmful insects, food-harmful insects, and so on. Typical examples of the pests include Lepidoptera such as Indian meal moth, and so on; Diptera such as Culex spp., Anopheles spp., Aedes spp., Muscidae, and so on; Coleoptera such as maize weevil, adzuki-bean weevil, red flour beetle, Anobiidae, powder post beetles, robe beetle, and so on; Dictyoptera such as German cockroach, smokybrown cockroach, American cockroach, brown cockroach, oriental cockroach, and so on; Hymenoptera such as ants, Bethylid, and so on; Siphonaptera such as human flea, cat flea, dog flea, and so on; Anoplura such as human louce, crab louce, and so on; Isoptera such as japanese termite, Formosan subterranean termite, and so on; house-dust mites such as Acaridae, Pyroglyphidae, Cheyetidae, and so on; Ornithonyssus spp.; ticks such as *Boophilus microplus,* and so on. The present pesticidal device is especially effective for controlling flies and mosquitoes.

The present pesticidal device, moreover, may hold synergists such as piperonyl butoxide, octachlorodipropyl ether, cynepyrin 222, cynepyrin 500, and so on, antioxidants such as dibutylhydroxytoluene, butylhydroxyanisole, 2,2'- methylenebis(4-methyl-6-tert-butylphenol), BHT, octadecyl 3-(3,3-di-tert-butyl-4-hydroxyphenyl)propionate, and soon, phosphite antioxidants, sulfer antioxidants, hindered amine light stabilizers, acid scavengers such as epoxy-soybean oil, and so on, stabilizers such as UV-stabilizers, esters such as isopropyl myristate, ethyl stearate, dibutyl adipate, dibutyl phthalate, etc. on the balloon material.

EXAMPLES

The following examples further illustrate the present invention in detail.

Example 1

On the surface of a rubber balloon on the market, a 10% ethanol solution of 1-ethynyl-2-fluoro-2-pentenyl (1R)trans-3-(2,2-dichlorovinyl)-2,2-dimethylcyclopropanecarboxylate (20 ml) is painted and then dried to obtain a present pesticidal device.

Example 2

On the surface of a paper balloon on the market, a 10% ethanol solution of 1-ethynyl-2-fluoro-2-pentenyl (1R)-trans-3-(2,2-dichlorovinyl)-2,2-dimethylcyclopropanecarboxylate (10 ml) is painted and then dried to obtain a present pesticidal device.

Example 3

The pesticidal device produced in Example 1 is swollen to about 30 cm in diameter and set in a room to repel flies and mosquitos.

Example 4

The pesticidal device produced in Example 2 is swollen to about 20 cm in diameter and set in a room to repel flies and mosquitos.

Example 5

On the surface of a rubber balloon on the market, a 10% ethanol solution of (RS)-1-ethynyl-2-methyl-2-pentenyl (EZ)-(1R)-trans-3-(2-chloro-2-fluorovinyl)-2,2-dimethylcyclopropane- 1-carboxylate (20 ml) is painted and then dried to obtain a present pesticidal device.

Example 6

On the surface of a paper balloon on the market, a 10% ethanol solution of (RS)-1-ethynyl-2-methyl-2-pentenyl (EZ)-(1R)-trans-3-(2-chloro-2-fluorovinyl)-2,2-dimethylcyclopropane-1-carboxylate (10 ml) is painted and then dried to obtain a present pesticidal device.

Example 7

The pesticidal device produced in Example 5 is swollen to about 30 cm in diameter and set in a room to repel flies and mosquitos.

Example 8

The pesticidal device produced in Example 6 is swollen to about 20 cm in diameter and set in a room to repel flies and mosquitos.

Example 9

On the surface of a rubber balloon on the market, a 10% ethanol solution of 2,3,5,6-tetrafluoro-4-methylbenzyl (1R)-trans-3-(2-methyl-1-propenyl)-2,2-dimethylcyclopropanecarboxylate (20 ml) is painted and then dried to obtain a present pesticidal device.

Example 10

On the surface of a paper balloon on the market, a 10% ethanol solution of 2,3,5,6-tetrafluoro-4-methylbenzyl (1R)-trans-3-(2-methyl-1-propenyl)-2,2-dimethylcyclopropanecarboxylate (10 ml) is painted and then dried to obtain a present pesticidal device.

Example 11

The pesticidal device produced in Example 9 is swollen to about 30 cm in diameter and set in a room to repel flies and mosquitos.

Example 12

The pesticidal device produced in Example 10 is swollen to about 20 cm in diameter and set in a room to repel flies and mosquitos.

Example 13

On the surface of a rubber balloon on the market, a 10% ethanol solution of 2,3,5,6-tetrafluoro-4-methylbenzyl (1R)-trans-3-(2-chloro-2-fluorovinyl)-2,2-dimethylcyclopropanecarboxylate (20 ml) is painted and then dried to obtain a present pesticidal device.

Example 14

On the surface of a paper balloon on the market, a 10% ethanol solution of 2,3,5,6-tetrafluoro-4-methylbenzyl (1R)-trans-3-(2-chloro-2-fluorovinyl)-2,2-dimethylcyclopropanecarboxylate (10 ml) is painted and then dried to obtain a present pesticidal device.

Example 15

The pesticidal device produced in Example 13 is swollen to about 30 cm in diameter and set in a room to repel flies and mosquitos.

Example 16

The pesticidal device produced in Example 14 is swollen to about 20 cm in diameter and set in a room to repel flies and mosquitos.

Example 17

On the surface of a rubber balloon on the market, a 10% ethanol solution of 2,3,5,6-tetrafluoro-4-methylbenzyl (1R)-trans-3-((Z)-1-propenyl)-2,2-dimethylcyclopropanecarboxylate (20 ml) is painted and then dried to obtain a present pesticidal device.

Example 18

On the surface of a paper balloon on the market, a 10% ethanol solution of 2,3,5,6-tetrafluoro-4-methylbenzyl (1R)-trans-3-((Z)-1-propenyl)-2,2-dimethylcyclopropanecarboxylate (10 ml) is painted and then dried to obtain a present pesticidal device.

Example 19

The pesticidal device produced in Example 17 is swollen to about 30 cm in diameter and set in a room to repel flies and mosquitos.

Example 20

The pesticidal device produced in Example 18 is swollen to about 20 cm in diameter and set in a room to repel flies and mosquitos.

What is claimed is:

1. A pesticidal device which comprises a pesticidal ingredient which is volatile at room temperature is supported on a balloon material swollen by gas.

2. The pesticidal device according to claim 1, wherein the pesticidal ingredient is 1-ethynyl-2-fluoro-2-pentenyl 3-(2,2-dichlorovinyl)-2,2-dimethylcyclopropanecarboxylate.

3. The pesticidal device according to claim 1, wherein the pesticidal ingredient is 1-ethynyl-2-methyl-2-pentenyl 3-(2-chloro-2-fluorovinyl)-2,2-dimethylcyclopropanecarboxylate.

4. The pesticidal device according to claim 1, wherein the pesticidal ingredient is 2,3,5,6-tetrafluoro-4-methylbenzyl 3-(2-methyl-1-propenyl)-2,2-dimethylcyclopropanecarboxylate.

5. The pesticidal device according to claim 1, wherein the pesticidal ingredient is 2,3,5,6-tetrafluoro-4-methylbenzyl 3-(2-chloro-2-fluorovinyl)-2,2-dimethylcyclopropanecarboxylate.

6. The pesticidal device according to claim 1, wherein the pesticidal ingredient is 2,3,5,6-tetrafluoro-4-methylbenzyl 3-(1-propenyl)-2,2-dimethylcyclopropanecarboxylate.

7. The pesticidal device according to claim 1, 2, 3, 4, 5 or 6, wherein the balloon material is made of rubber.

8. The pesticidal device according to claim 1, 2, 3, 4, 5 or 6, wherein the balloon material is made of paper.

9. A pesticidal method which comprises supporting a pesticidal ingredient which is volatile at room temperature with a balloon swollen by gas.

* * * * *